US011801125B2

(12) United States Patent
Huang et al.

(10) Patent No.: US 11,801,125 B2
(45) Date of Patent: Oct. 31, 2023

(54) RECONSTRUCTION PROSTHESIS

(71) Applicant: INDUSTRIAL TECHNOLOGY RESEARCH INSTITUTE, Hsinchu (TW)

(72) Inventors: Wei-Chin Huang, Tainan (TW); De-Yau Lin, Tainan (TW); Chuan-Sheng Chuang, Tainan (TW); An-Li Chen, Tainan (TW); Bo Min Xu, Kaohsiung (TW); Chun-Feng Chen, Kaohsiung (TW); Sung-Ho Liu, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 227 days.

(21) Appl. No.: 16/725,502

(22) Filed: Dec. 23, 2019

(65) Prior Publication Data
US 2021/0121269 A1 Apr. 29, 2021

(30) Foreign Application Priority Data

Oct. 23, 2019 (TW) ................................ 108138259

(51) Int. Cl.
*A61C 8/00* (2006.01)
(52) U.S. Cl.
CPC ............ *A61C 8/0095* (2013.01); *A61C 8/005* (2013.01); *A61C 8/0065* (2013.01); *A61C 8/0086* (2013.01)

(58) Field of Classification Search
CPC .............. A61C 13/0001; A61C 8/0095; A61C 13/0004; A61C 13/0022; A61C 8/0012; A61C 8/0057; A61C 8/0062; A61C 8/0065; A61C 9/002; A61C 13/34; A61C 8/0027; A61C 8/0043; A61C 8/0006;
(Continued)

(56) References Cited

U.S. PATENT DOCUMENTS

| 3,488,779 A | 1/1970 | Christensen |
| 3,683,422 A | 8/1972 | Stemmer et al. |

(Continued)

FOREIGN PATENT DOCUMENTS

| CN | 102905644 A | 1/2013 | |
| DE | 102011014664 A1 * | 3/2012 | ........... A61C 9/0093 |

(Continued)

OTHER PUBLICATIONS

TW Office Action in Application No. 108138259 dated Mar. 3, 2020.

(Continued)

*Primary Examiner* — Jacqueline T Johanas
*Assistant Examiner* — Shannel Nicole Belk
(74) *Attorney, Agent, or Firm* — Maschoff Brennan

(57) ABSTRACT

The disclosure relates to a reconstruction prosthesis including a plurality of prosthesis units connected in series. Each of the prosthesis units includes a main part and a cushion structure. The main part has an abutment insertion opening and an accommodation space. The cushion structure is located in the accommodation space and movably located at the abutment insertion opening and defining an abutment mounting hole connected to the abutment insertion opening. The cushion structure is deformable with respect to the main part.

12 Claims, 10 Drawing Sheets

(58) Field of Classification Search
CPC .... A61C 8/0086; A61F 2/3099; A61F 2/2803; A61F 2/2846; A61F 2002/2839; A61F 2002/285
USPC .......................................................... 433/213
See application file for complete search history.

(56) References Cited

U.S. PATENT DOCUMENTS

| | | | |
|---|---|---|---|
| 3,720,959 | A | 3/1973 | Hahn |
| 4,636,215 | A | 1/1987 | Schwartz |
| 4,693,722 | A | 9/1987 | Wall |
| 4,726,808 | A | 2/1988 | Collins |
| 4,778,472 | A | 10/1988 | Homsy et al. |
| 5,213,500 | A * | 5/1993 | Salazar ................ A61C 8/0018 433/169 |
| 5,425,639 | A * | 6/1995 | Anders ................ A61C 8/0086 433/169 |
| 5,489,305 | A | 2/1996 | Morgan |
| 5,975,904 | A | 11/1999 | Spiegel |
| 6,060,641 | A * | 5/2000 | Manolidis ............ A61F 2/2803 128/898 |
| 6,325,803 | B1 * | 12/2001 | Schumacher ...... A61B 17/8047 606/104 |
| 9,943,410 | B2 | 4/2018 | Hollister et al. |
| 10,166,054 | B2 | 1/2019 | Woodburn, Sr. et al. |
| 10,219,848 | B2 * | 3/2019 | Leuenberger ...... A61B 17/8071 |
| 2008/0228278 | A1 * | 9/2008 | Lee ...................... A61C 8/0018 623/17.17 |
| 2015/0118647 | A1 | 4/2015 | Skvirsky et al. |
| 2017/0325916 | A1 | 11/2017 | Sunavala-Dossabhoy et al. |
| 2018/0206944 | A1 | 7/2018 | Lomicka et al. |
| 2019/0070006 | A1 * | 3/2019 | Goh ...................... A61F 2/2803 |
| 2020/0315749 | A1 * | 10/2020 | Kim ...................... A61C 8/0057 |

FOREIGN PATENT DOCUMENTS

| | | | | |
|---|---|---|---|---|
| EP | 2143398 A1 * | 1/2010 | ............ | A61C 8/005 |
| EP | 1940303 B1 | 10/2014 | | |
| KR | 2017-0088871 A | 8/2017 | | |
| TW | I252112 B | 4/2006 | | |
| WO | 2007/061382 A1 | 5/2007 | | |

OTHER PUBLICATIONS

Ren et al. "Virtual Planning and 3D printing modeling for mandibular reconstruction with fibula free flap" Med Oral Patol Oral Cir Bucal. May 1, 2018;23 (3):e359-66.

A. Dupret-Bories et al. "Contribution of 3D printing to mandibular reconstruction after cancer" European Annals of Otorhinolaryngology, Head and Neck diseases; vol. 135, Issue 2, Apr. 2018, pp. 133-136.

Moiduddin et al. "Digital Design, Analysis and 3D Printing of Prosthesis Sca olds for Mandibular Reconstruction" Metals, May 2019, 9, 569; doi: 10.3390/met9050569.

Mehle et al. "Evaluation of a New PEEK Mandibular Reconstruction Plate Design for Continuity Defect Therapy" International Journal of New Technology and Research (IJNTR) ISSN:2454-4116, vol. 2, Issue-7, Jul. 2016 pp. 65-71.

T. Sella-Tunis et al. "Human mandibular shape is associated with masticatory muscle force" Scientific Reports vol. 8, Article No. 6042; Apr. 16, 2018.

Kwon et al. "Newly designed retentive posts of mandibular reconstruction plate in oral cancer patients based on preliminary FEM study" World Journal of Surgical Oncology; 14:292; Nov. 21, 2016.

* cited by examiner

RECONSTRUCTION PROSTHESIS

CROSS-REFERENCE TO RELATED APPLICATIONS

This non-provisional application claims priority under 35 U.S.C. § 119(a) on Patent Application No(s). 108138259 filed in R.O.C. Taiwan on Oct. 23, 2019, the entire contents of which are hereby incorporated by reference.

TECHNICAL FIELD

The disclosure relates to a prosthesis, more particularly to a reconstruction prosthesis.

BACKGROUND

In recent years, the incidence of oral, oropharyngeal and hypopharyngeal malignant tumors largely increases. In severe cases, the tumor and nearby tissues have to be removed. However, considering those who have a large range of tissues been removed, the wound cannot be directly sutured and will result in severe maxillary or mandibular defects and tissue dysfunction, then a tissue reconstruction surgery becomes a necessity to reconstruct the facial defect.

Taking the mandible reconstruction as an example, the conventional reconstruction is commonly performed through a fibula free flap procedure. The fibula flap takes bone and its corresponding blood vessels from the patient's lower leg and uses it to rebuild the structures of the mandibular defects or missing mandibular bone. However, the fibula flap procedure still has disadvantages. For example, the harvested fibula fragments and the mandibular defects and missing segments are quite different in size and geometry so that the fibular usually fails to match the mandibular defects or missing mandibular bone and still will result in severe facial defects. Also, the harvested fibula does not have the ability to distribute or absorb pressure, such that the patient's mandible is unable to withstand the pressure caused by dental implant surgery or occlusion. In other words, the patient who had undergone the fibula flap procedure will be unable to take dental implant surgery to replace missing teeth. The absence of teeth makes the facial defects more obvious.

Therefore, some begun to use 3D printing technology to produce a metal prosthesis matching the mandibular defects or missing mandibular bone, it is still unable to overcome the above pressure issues. According to references, during the dental implant surgery or occlusion, the pressure on the conventional metal mandibular prosthesis cannot be distributed and reduced and always results in stress concentration. This often easily causes the parts of the prosthesis, in which the stress concentration occurs or the nearby osseous tissue contacts, to deform or collapse.

SUMMARY

One embodiment of the disclosure provides a reconstruction prosthesis including a plurality of prosthesis units connected in series. Each of the prosthesis units includes a main part and a cushion structure. The main part has an abutment insertion opening and an accommodation space. The cushion structure is located in the accommodation space and movably located at the abutment insertion opening and defining an abutment mounting hole connected to the abutment insertion opening. The cushion structure is deformable with respect to the main part.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

Figure 1:
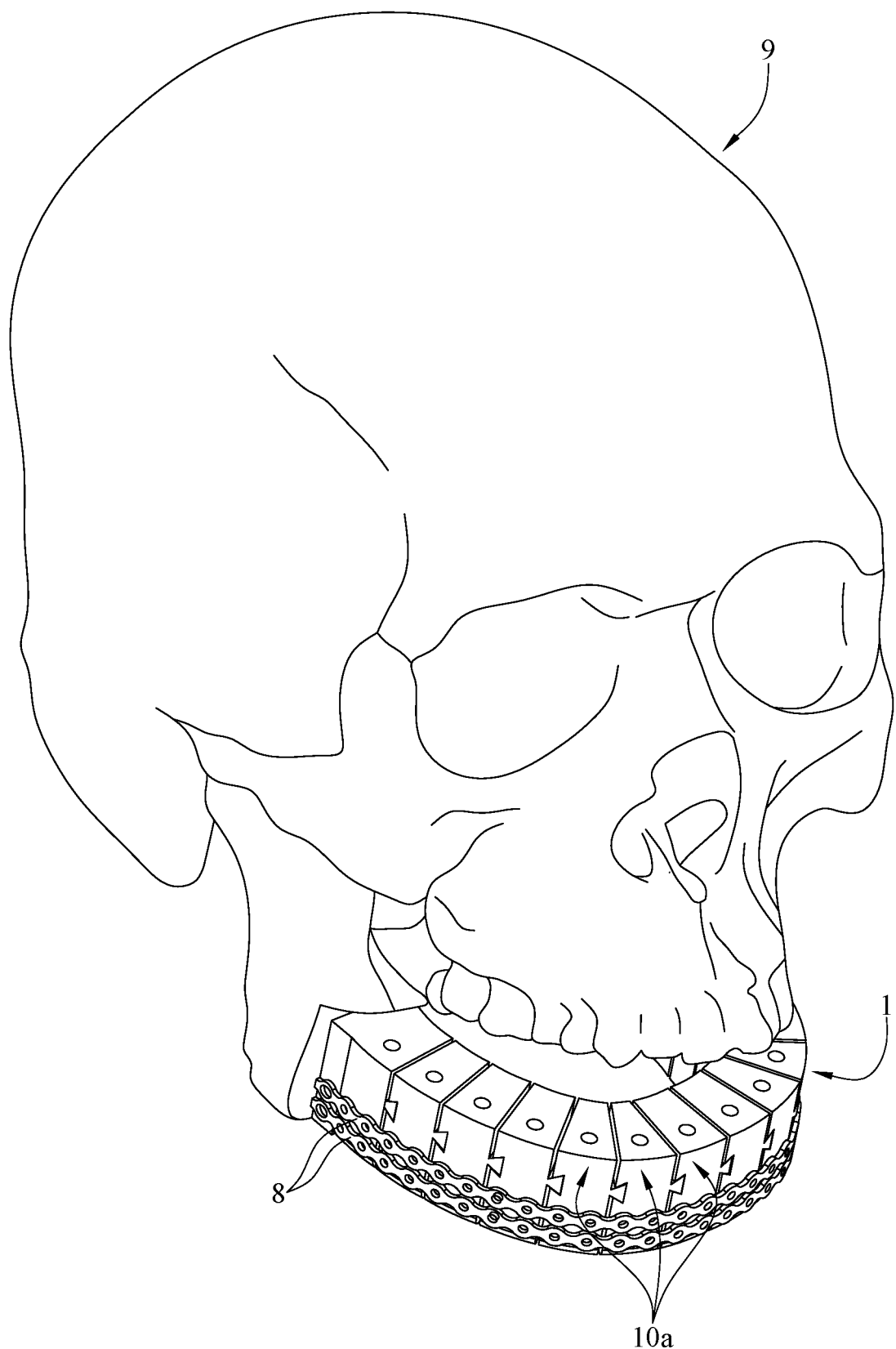
FIG. 1 depicts a reconstruction prosthesis according to one embodiment of the disclosure used in the mandibular bone.

In the following detailed description, for purposes of explanation, numerous specific details are set forth in order to provide a thorough understanding of the disclosed embodiments. It will be apparent, however, that one or more embodiments may be practiced without these specific details.

In addition, for the purpose of simple illustration, well-known features may be drawn schematically, and some unnecessary details may be omitted from the drawings. And the size or ratio of the features in the drawings of the present disclosure may be exaggerated for illustrative purposes, but the present disclosure is not limited thereto. Note that the actual size and designs of the product manufactured based on the teaching of the present disclosure may also be properly modified according to any actual requirement.

Further, as used herein, the terms "end", "part", "portion" or "area" may be used to describe a technical feature on or between component(s), but the technical feature is not limited by these terms. In addition, unless otherwise specified, the term "substantially", "approximately" or "about" may be used herein to provide an industry-accepted tolerance to its corresponding term without resulting in a change in the basic function of the subject matter at issue.

Furthermore, unless otherwise defined, all the terms used in the disclosure, including technical and scientific terms, have their ordinary meanings that can be understood by those skilled in the art. Moreover, the definitions of the above terms are to be interpreted as being consistent with the technical fields related to the disclosure. Unless specifically defined, these terms are not to be construed as too idealistic or formal meanings.

Figure 2:
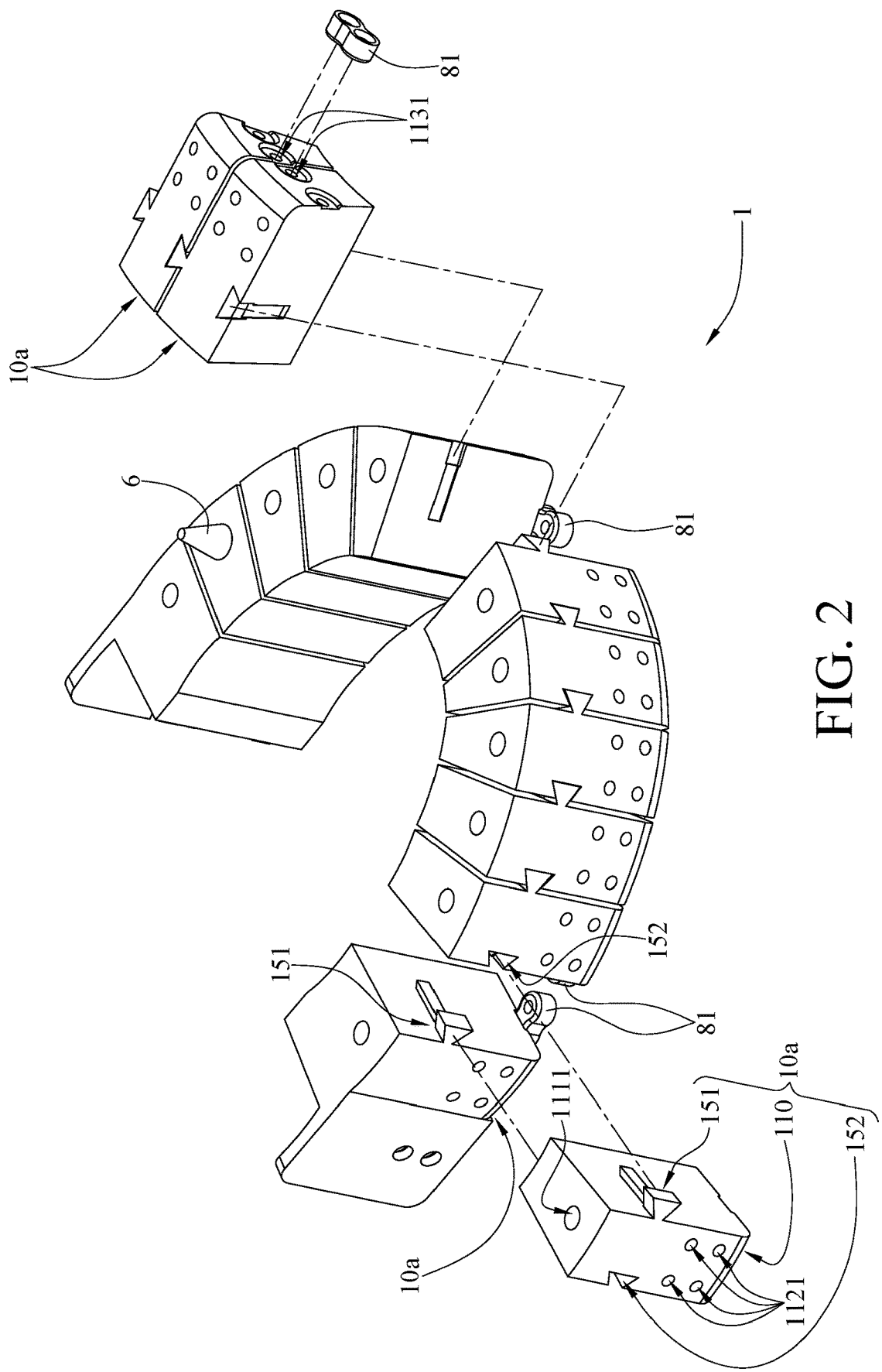
FIG. 2 is an exploded view of the reconstruction prosthesis in FIG. 1.

Firstly, please refer to FIGS. 1-2, where FIG. 1 depicts a reconstruction prosthesis 1 according to one embodiment of the disclosure used in mandibular bone, and FIG. 2 is an exploded view of the reconstruction prosthesis 1 in FIG. 1. As shown, the reconstruction prosthesis 1 is suitable to be implanted into human body to replace the missing segments (e.g., the space between the osseous tissues 9). Specifically, the reconstruction prosthesis 1 is configured for the reconstruction of facial bone, such as maxillary or mandibular defects or missing maxillary or mandibular bone. While the present disclosure will mainly be described with reference to the mandibular defects reconstruction but the present disclosure is not limited thereto. For instance, the present disclosure may be advantageously used in maxillary bone reconstruction.

In this and some other embodiments, the reconstruction prosthesis 1 at least includes one or more prosthesis units 10a that are similar or the same in configuration. These prosthesis units 10a can be detachably connected in series. As shown, the prosthesis unit 10a at least includes a main part 110, a first engagement portion 151, and a second engagement portion 152. The main part 110 is, for example, a hollow block. The first engagement portion 151 and the second engagement portion 152 are respectively located at two opposite sides of the main part 110 and are a convex structure and a mating concave structure. In this embodiment, the first engagement portion 151 is, for example, a dovetail shaped protrusion, and the second engagement portion 152 is, for example, a dovetail shaped recess capable of being engaged with the first engagement portion 151. As such, the adjacent prosthesis units 10a can be detachably engaged with each other via their first engagement portion 151 and second engagement portion 152. However, the disclosure is not limited by the first engagement portion 151, the second engagement portion 152, and their designs; for example, in some other embodiments, the first engagement portion and the second engagement portion of the prosthesis unit may be a convex structure and a mating concave structure that are in other shapes; alternatively, in another embodiment, the prosthesis unit may not have the aforementioned first engagement portion and second engagement portion.

In addition, in the reconstruction prosthesis 1, the quantity of the prosthesis units 10a may be determined by the actual condition of the mandibular defects or missing mandibular bone. It is understood that more mandibular defects or missing mandibular bone require more amount of the prosthesis units 10a.

Also, to fit the mandibular defects or missing mandibular bone, the shape of the prosthesis unit 10a may be modified accordingly. As shown in FIG. 1, the prosthesis units 10a of the reconstruction prosthesis 1 may form a U-shape or C-shape assembly, but the disclosure is not limited to the size or shape of each prosthesis unit 10a. In some embodiments, the prosthesis unit 10a may be smaller or bigger, or may have a size or shape different from the adjacent ones. For example, the prosthesis unit 10a may be in cylindrical shape or other suitable shapes.

In addition, in this and some other embodiments, each prosthesis unit 10a of the reconstruction prosthesis 1 is, for example, a single piece and is made of biocompatible material, such as titanium alloy, iron-based alloy, cobalt alloy, polymer material, ceramic or composite material thereof, but the disclosure is not limited thereto. In addition, in this and some other embodiments, the prosthesis unit 10a is manufactured by 3D printing, this avoids taking the autologous bone as a prosthesis, and the appearance of the 3D printed prosthesis units 10a can be customized so that the reconstruction prosthesis 1 can be shaped and sized to match the actual conditions of the mandibular defects or missing mandibular bone. Therefore, the reconstruction prosthesis 1 is highly flexible in design and can be customized to optimally reconstruct the mandible to reduce the effect on the patient's facial appearance.

As shown, in this and some other embodiments, each prosthesis unit 10a of the reconstruction prosthesis 1 has at least one abutment insertion opening 1111 configured for the insertion of an abutment fastener 7a of an abutment 6. Note that the abutment 6 is the piece that connects the prosthesis unit 10a and the crown (not shown). However, the disclosure is not limited to the abutment, and its material and design.

Further, in this and some other embodiments, in the reconstruction prosthesis 1, each of the prosthesis units 10a further has at least one reconstruction plate mounting hole 1121 configured for the fixation of at least one reconstruction plate 8. The reconstruction plate 8 can be fixed to the reconstruction plate mounting hole 1121 via one or more screws (not shown). Therefore, the prosthesis units 10a of the reconstruction prosthesis 1 may be connected via the reconstruction plate 8. The reconstruction plate 8 is able to strengthen the connection among these prosthesis units 10a. In addition, the ends of the reconstruction plate 8 may be fixed to the nearby osseous tissues 9 so as to fix the assembly of the prosthesis units 10a in a proper position with respect to the osseous tissues 9, such that the abutment 6 fixed on the reconstruction prosthesis 1 can be arranged in the desired position. However, the disclosure is not limited to the reconstruction plate mounting hole 1121 and its quantity and design. In some embodiments, the prosthesis unit 10a may not have the aforementioned reconstruction plate mounting hole 1121, in such a case, the prosthesis unit 10a may be directly fixed to the osseous tissue 9 via screws or other suitable means.

In addition, as shown in FIG. 2, each prosthesis unit 10a of the reconstruction prosthesis 1 has at least one screw hole 1131. In this embodiment, each prosthesis unit 10a has two screw holes 1131 respectively corresponding to that of the adjacent prosthesis units 10a. A connecting component 81 can be fixed to the screw holes 1131 on two adjacent prosthesis units 10a via screws (not shown), such that the adjacent prosthesis units 10a can be fixed to each other. The connecting component 81 can further improve the structural strength of the reconstruction prosthesis 1. However, the screw hole 1131 and the connecting component 81 may be optional; in some other embodiments, the prosthesis unit 10a may not have the screw holes 1131 and the connecting component 81.

In this and some other embodiments, the prosthesis unit 10a is able to absorb impact and vibration applied on the abutment 6 so as to reduce the pressure occurring during occlusion, thereby preventing the stress concentration from occurring at the reconstruction prosthesis 1 or the contact surface between the reconstruction prosthesis 1 and the osseous tissue 9.

Figure 3A:
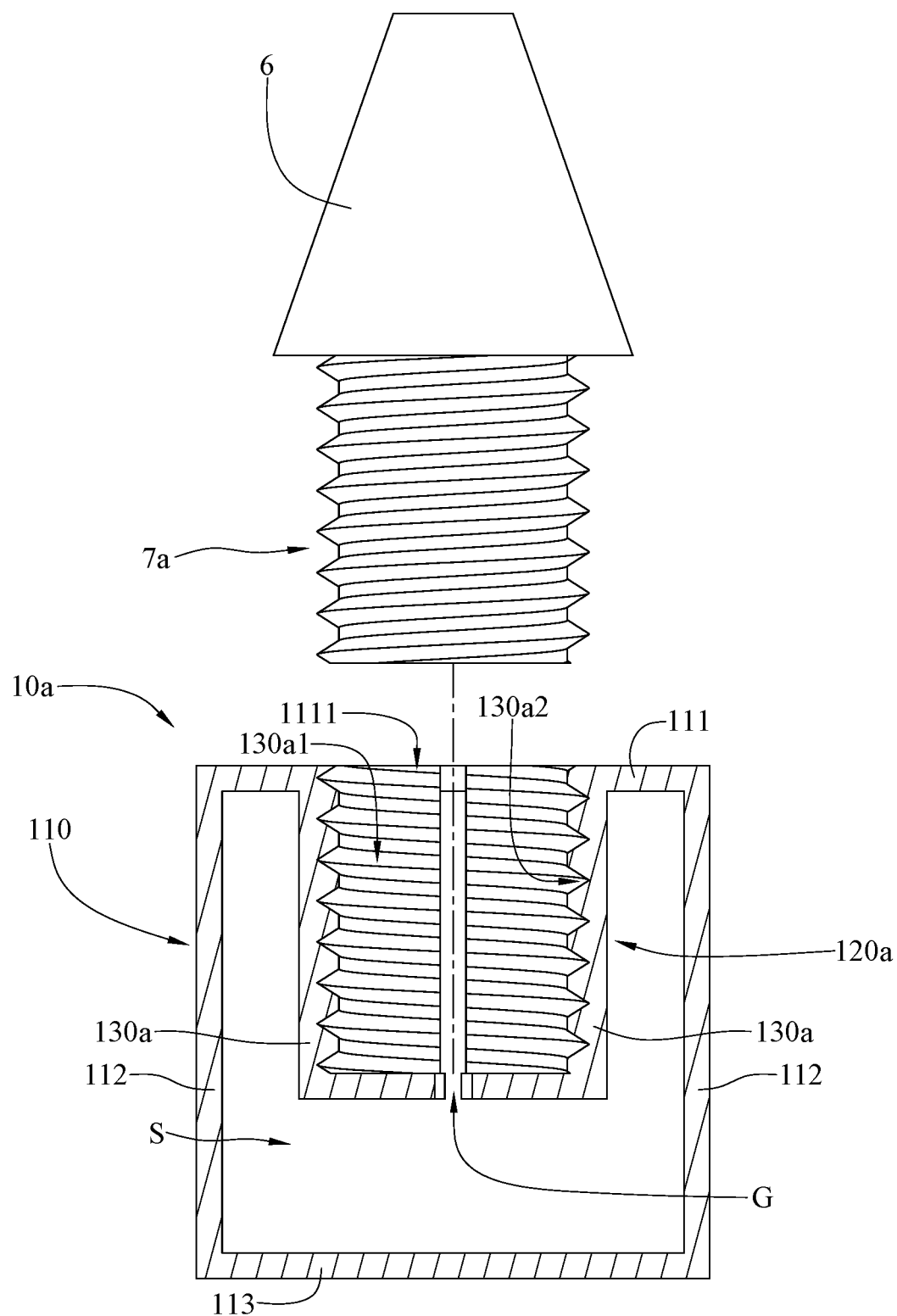
FIG. 3A is a cross-sectional side view of the prosthesis unit in FIG. 2.
Figure 3B:
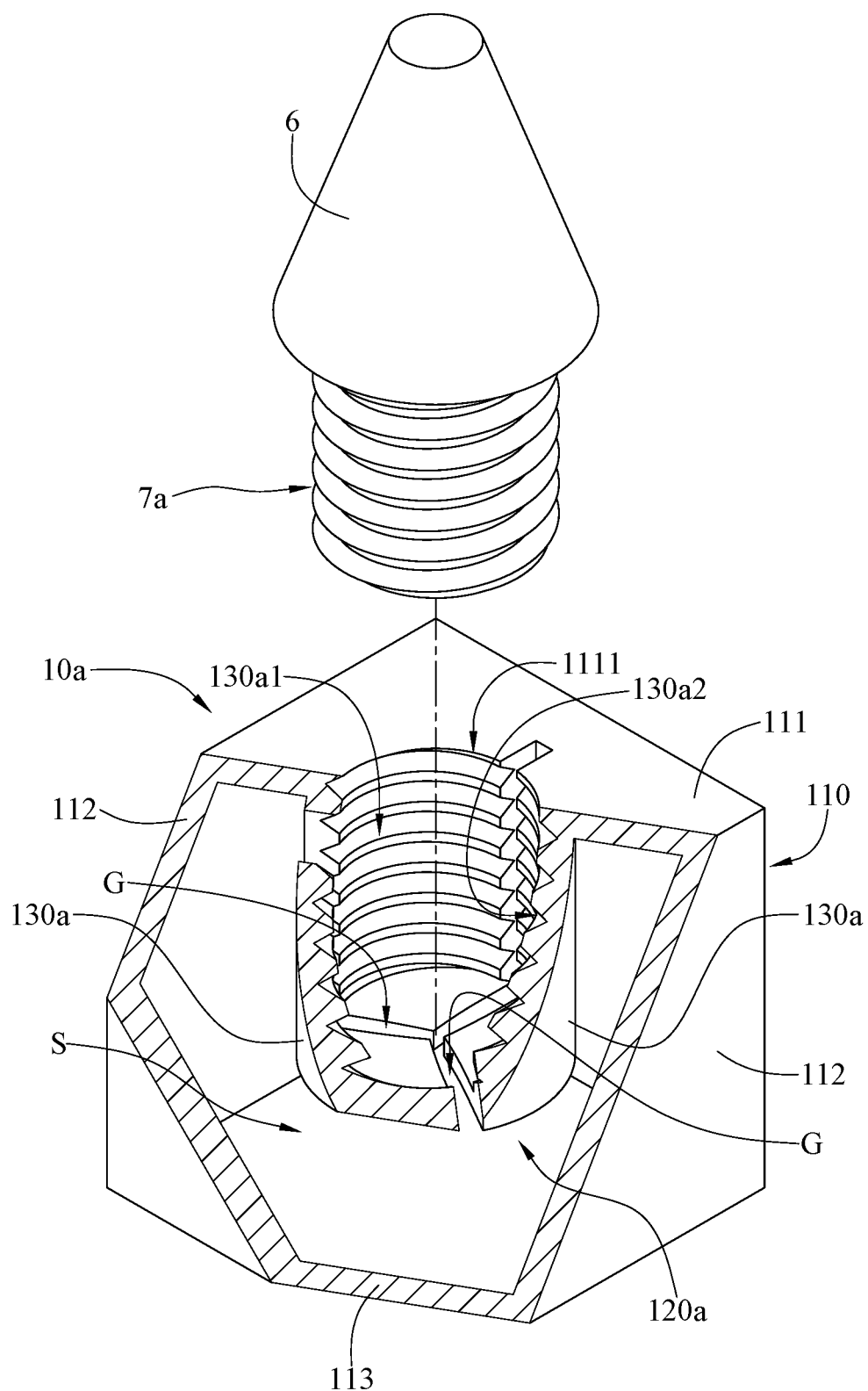
FIG. 3B is a partially cross-sectional perspective view of the prosthesis unit in FIG. 2.

Referring to FIGS. 3A-3B, where FIG. 3A is a cross-sectional side view of the prosthesis unit 10a in FIG. 2, and FIG. 3B is a partially cross-sectional perspective view of the prosthesis unit 10a in FIG. 2. In this and some other embodiments, the main part 110 of the prosthesis unit 10a includes a top plate 111, a plurality of side plate 112, and a bottom plate 113. The top plate 111 is located opposite to the bottom plate 113, and the side plates 112 are connected to and located between the top plate 111 and the bottom plate 113. The top plate 111, the side plates 112, and the bottom plate 113 together form an internal space S therebetween.

In this embodiment, the aforementioned abutment insertion opening 1111 is formed on the top plate 111, the aforementioned reconstruction plate mounting hole 1121 is formed on one of the side plates 112, and the aforementioned screw hole 1131 is formed on the bottom plate 113. However, for the purpose of simple illustration, the reconstruction plate mounting hole 1121 and screw hole 1131 are omitted from FIGS. 3A and 3B or later drawings.

In addition, in this or some other embodiments, the prosthesis unit 10a further includes a cushion structure 120a located in the internal space S of the main part 110 and is movably connected to the abutment insertion opening 1111. Specifically, in this embodiment, the cushion structure 120a includes at least one abutment engagement portion 130a, as shown in FIGS. 3A and 3B, there are more than two abutment engagement portions 130a in the internal space S. The abutment engagement portions 130a extend inwards from the inner surface of the top plate 111 of the main part 1100. The abutment engagement portions 130a surround the abutment fastener 7a and together form an abutment mounting hole 130a1 connected to the abutment insertion opening 1111, in other words, the abutment mounting hole 130a1 defined by the abutment engagement portions 130a is exposed from the abutment insertion opening 1111 of the main part 110.

Therefore, the abutment 6 is allowed to be inserted into the abutment mounting hole 130a1 defined by the abutment engagement portions 130a through the abutment insertion opening 1111. Note that the inner wall (not numbered) of the abutment engagement portion 130a has an internal thread 130a2 mating the external thread on the abutment fastener 7a of the abutment 6. In this configuration, the abutment 6 can be engaged with the abutment engagement portions 130a of the prosthesis unit 10a.

In more detail, in this embodiment, the abutment engagement portions 130a of the cushion structure 120a are spaced apart by a given distance (e.g., a gap G shown in FIGS. 3A and 3B), thus these abutment engagement portions 130a are independent of one another and are not directly connected, such that each abutment engagement portion 130a can be considered as an elastic arm that may be deformed and moved with respect to the main part 110 as receives a certain amount of external force and may be return to its original shape when the force is removed. And the deformation of the abutment engagement portion 130a may not affect the other abutment engagement portions 130a. In such an arrangement, as an external force (e.g., the occlusal loading) is applied on the abutment 6 that is inserted into the abutment mounting hole 130a1 and engaged with the abutment engagement portions 130a, the abutment 6 may transfer the external force to the abutment engagement portions 130a and cause them to deform. The deformation of the abutment engagement portions 130a is able to absorb and reduce the external force, such that the impact or vibration to the abutment 6 is largely reduced. Accordingly, the stress concentration is prevented from occurring on the prosthesis unit 10a, and the prosthesis unit 10a is prevented from being dislocated. In contrast, the conventional mandible reconstruction prosthesis does not have any cushion structure to release impact and vibration so that it likely leads to issues, such as stress concentration and dislocation and is not able to take dental implant surgery.

Note that the disclosure is not limited to the quantity of the abutment engagement portions 130a that one prosthesis unit 10a may include; for example, in some other embodiments, one prosthesis unit 10a may include only two or more than two abutment engagement portions 130a. In addition, the length of the abutment engagement portion 130a may be modified according to actual requirements, and the disclosure is not limited thereto. Further, the disclosure is either not limited by how the abutment 6 is engaged with the abutment engagement portions 130a.

Figure 4A:
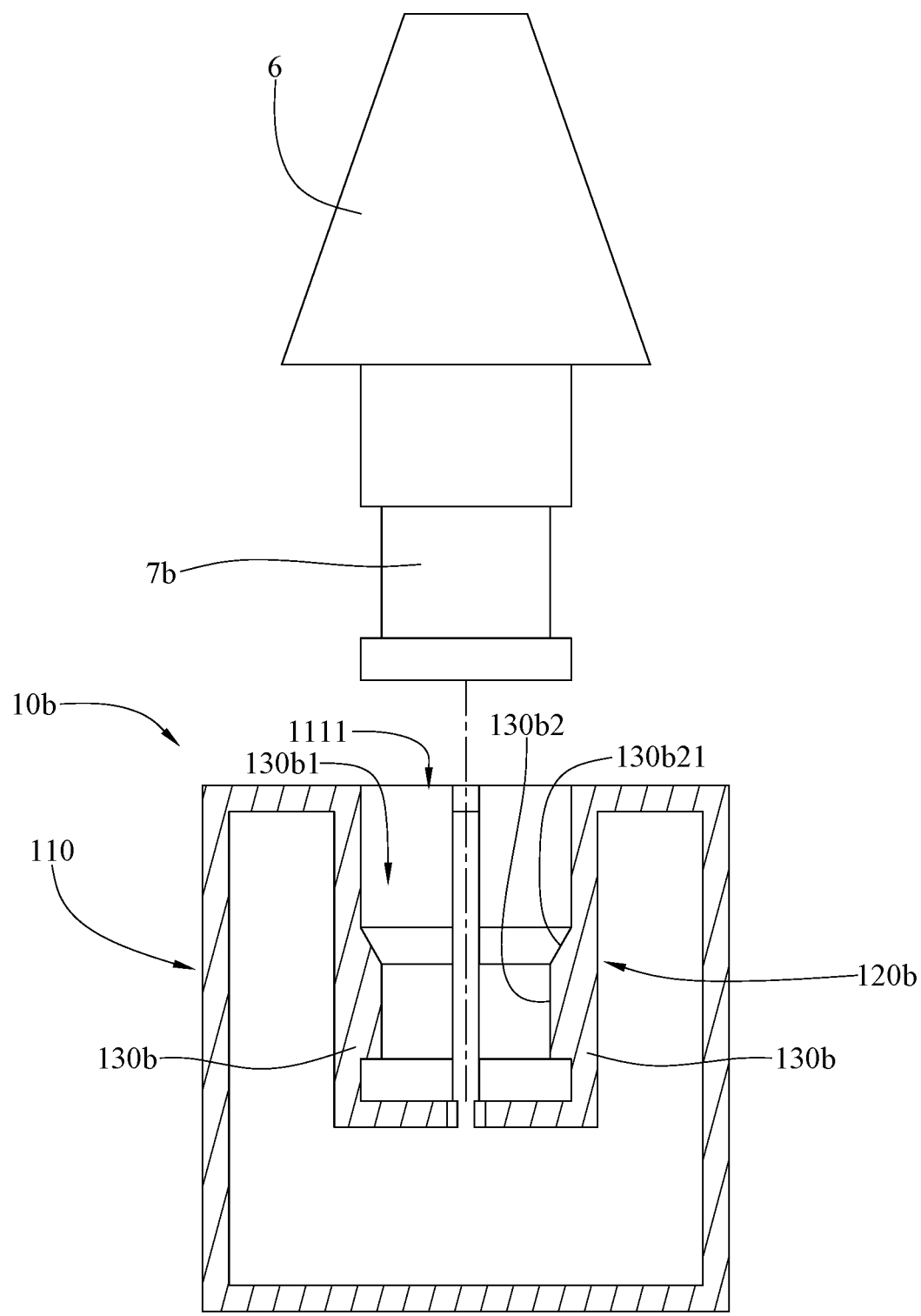
FIG. 4A is a cross-sectional side view of a prosthesis unit according to another embodiment of the disclosure.
Figure 4B:
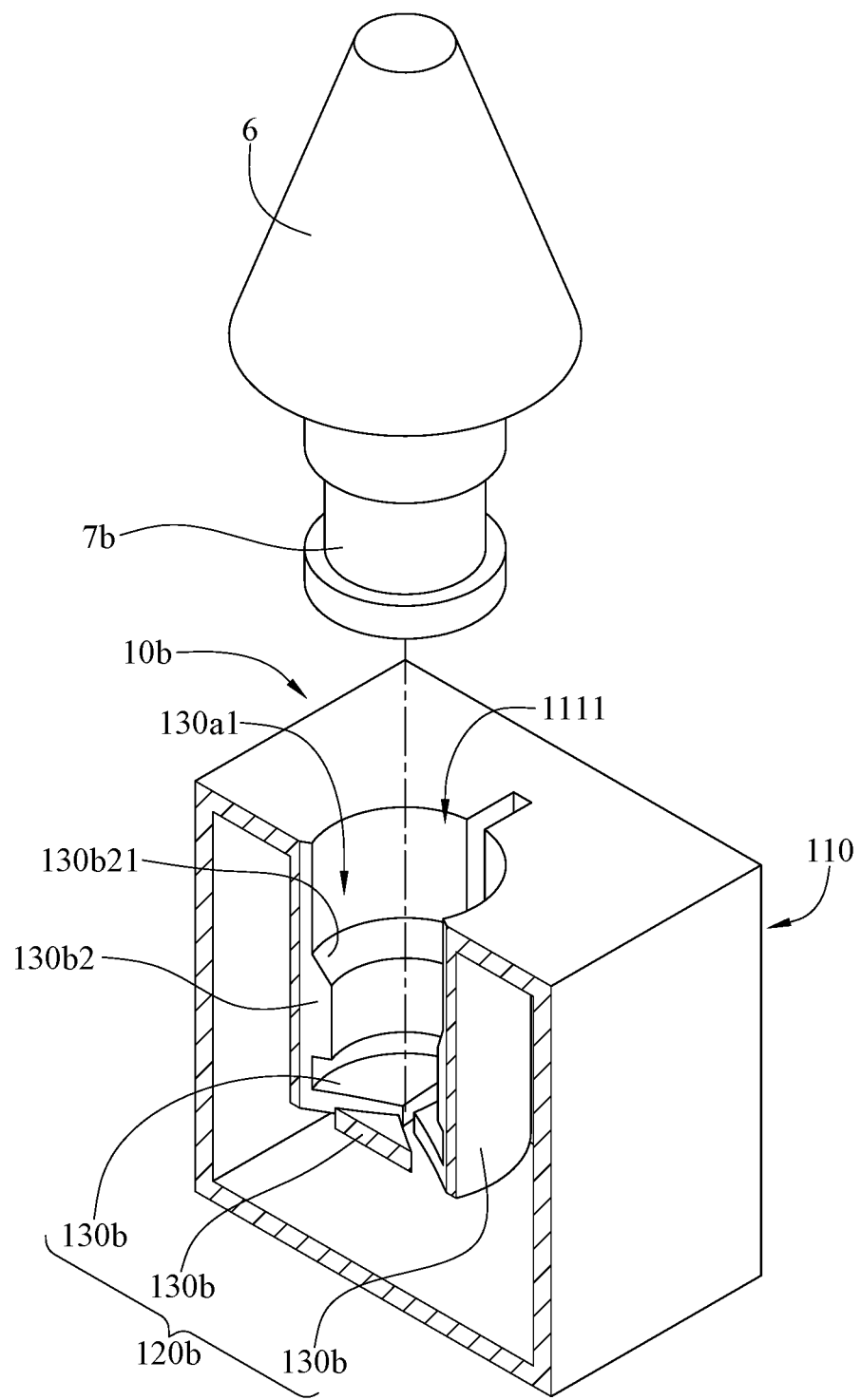
FIG. 4B is a partially cross-sectional perspective view of the prosthesis unit according to another embodiment of the disclosure.

For example, referring to FIGS. 4A-FIG. 4B, a cross-sectional side view and a partially cross-sectional perspective view of a prosthesis unit 10b according to another embodiment of the disclosure are provided. In this embodiment, each abutment engagement portion 130b of a cushion structures 120b of the prosthesis unit 10b has an inwardly protrusion 130b2, making the abutment mounting hole 130b1 defined by the abutment engagement portions 130b have a smaller diameter at the inwardly protrusion 130b2. Correspondingly, an abutment fastener 7b of the abutment 6 is in a form having a distal end of larger diameter and a neck of smaller diameter. In this configuration, the abutment fastener 7b may be plugged into the abutment mounting hole 130b1 and engaged with the abutment engagement portions 130b by being pushed inward. In normal use, the abutment engagement portions 130b are also able to absorb and reduce the impact or vibration to the abutment 6 and the prosthesis unit 10b. In more detail, the inwardly protrusion 130b2 has a guide slant 130b21 on a side of the inwardly protrusion 130b2 facing the abutment insertion opening 1111, which makes the abutment fastener 7b easier to push the inwardly protrusions 130b2 outward and slide over the inwardly protrusions 130b2 while inserting the abutment fastener 7b into the abutment mounting hole 130b1.

Figure 5A:
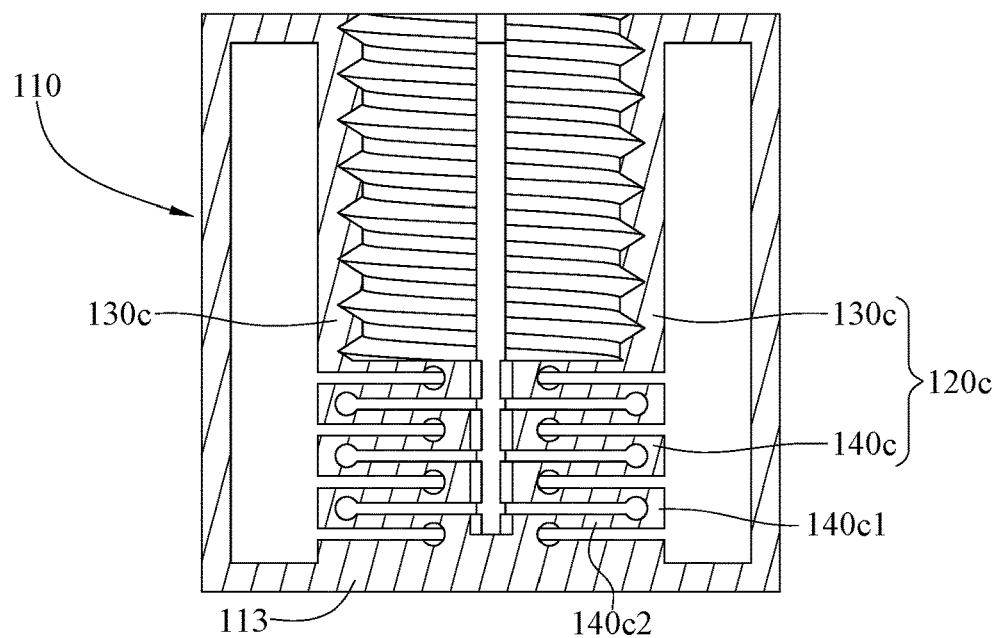
FIG. 5A is a cross-sectional side view of a prosthesis unit according to yet another embodiment of the disclosure.
Figure 5B:
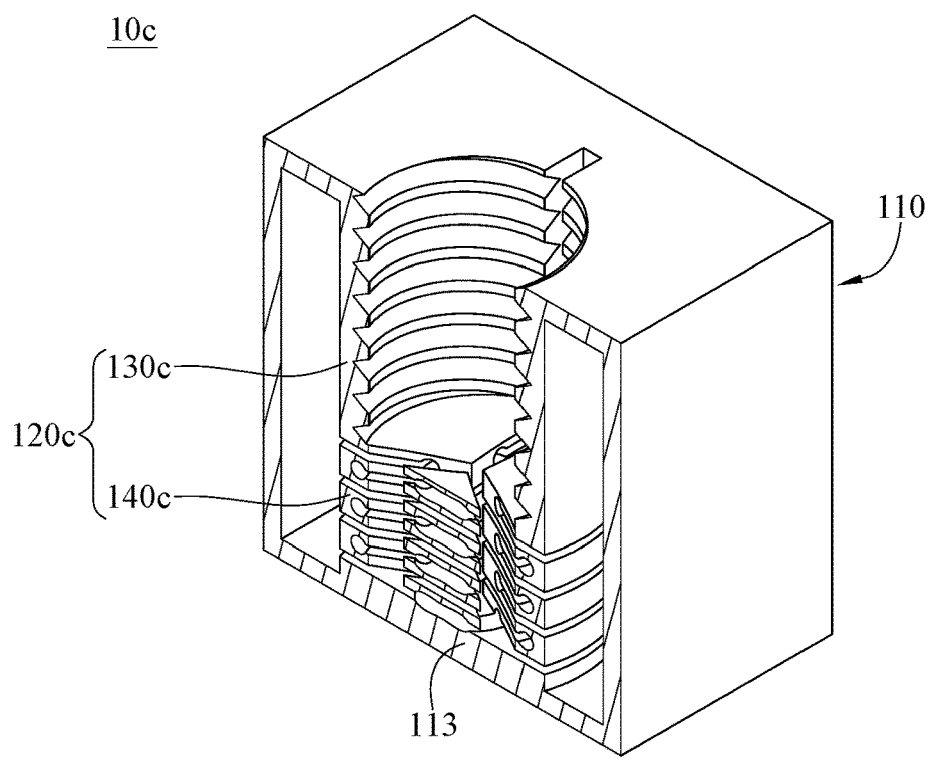
FIG. 5B is a partially cross-sectional perspective view of the prosthesis unit according to yet another embodiment of the disclosure.

In addition, the above cushion structures are merely the exemplary embodiments of the disclosure. Please refer to FIGS. 5A-5B, a cross-sectional side view and partially cross-sectional perspective view of a prosthesis unit 10c according to yet another embodiment of the disclosure are provided. In this embodiment, a cushion structure 120c of the prosthesis unit 10c includes a plurality of abutment engagement portions 130c and further includes at least one auxiliary cushioning portion 140c. The abutment engagement portion 130c may have the same or similar configuration to the aforementioned abutment engagement portion 130a, thus its descriptions will not be repeated below. The auxiliary cushioning portions 140c may be in the same amount as that of the abutment engagement portions 130c, and the auxiliary cushioning portions 140c are respectively arranged under the abutment engagement portions 130c. Specifically, the auxiliary cushioning portions 140 are respectively connected to the abutment engagement portions 130c, and the auxiliary cushioning portions 140 are connected to and located between the abutment engagement portions 130c and the bottom plate 113 of the main part 110.

In more detail, each auxiliary cushioning portion 140c is a serpentine structure that is flexible and compressible. More specifically, the auxiliary cushioning portion 140c includes a plurality of bend portions 140c1 and a plurality of suspended portions 140c2, wherein the suspended portions 140c2 are interconnected by the bend portions 140c1 at opposite ends so that the bend portions 140c1 and the suspended portions 140c2 together form a serpentine configuration capable of functioning as a compression spring. The auxiliary cushioning portion 140c is able to position the abutment engagement portion 130c with respect to the main part 110 and is also able to absorb and reduce the impact or vibration to the abutment engagement portion 130c, ensuring the prevention of the stress concentration.

In the auxiliary cushioning portion 140c, the quantities of the bend portions 140c1 and the suspended portions 140c2 may be modified according to actual requirements, such as the space size between the abutment engagement portions 130c and the bottom plate 113 of the main part 110 or the required elasticity and compressibility of the auxiliary cushioning portion 140c. In addition, not every abutment engagement portion 130c has the auxiliary cushioning portion 140c underneath. In some embodiments, there may be only one abutment engagement portions 130c supported by the auxiliary cushioning portion 140c; in such a case, the abutment engagement portion 130c supported by the auxiliary cushioning portion 140c may obtain a higher degree of restriction.

Figure 6A:
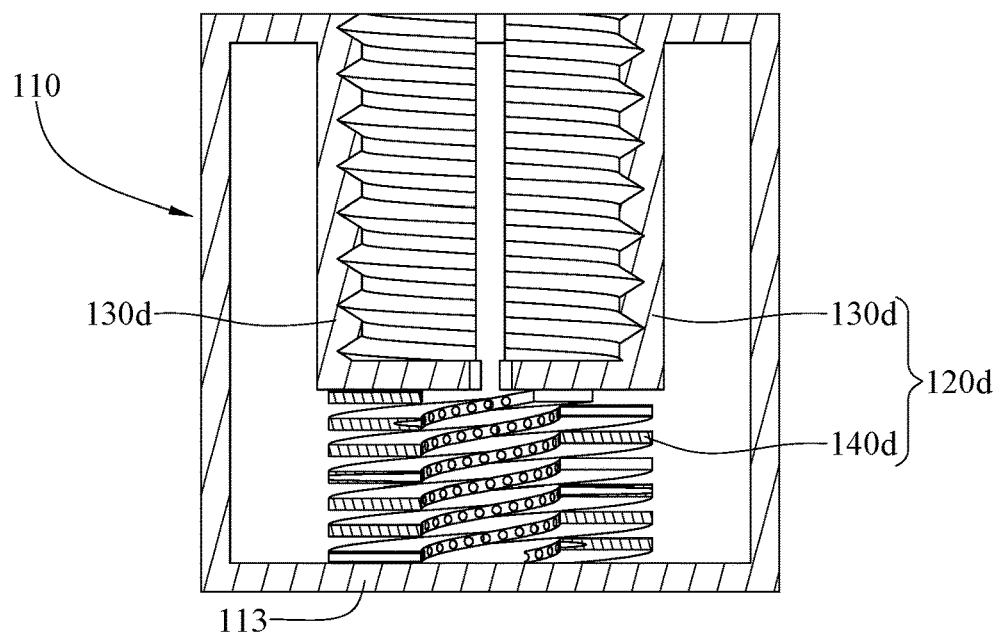
FIG. 6A is a cross-sectional side view of a prosthesis unit according to still another embodiment of the disclosure.
Figure 6B:
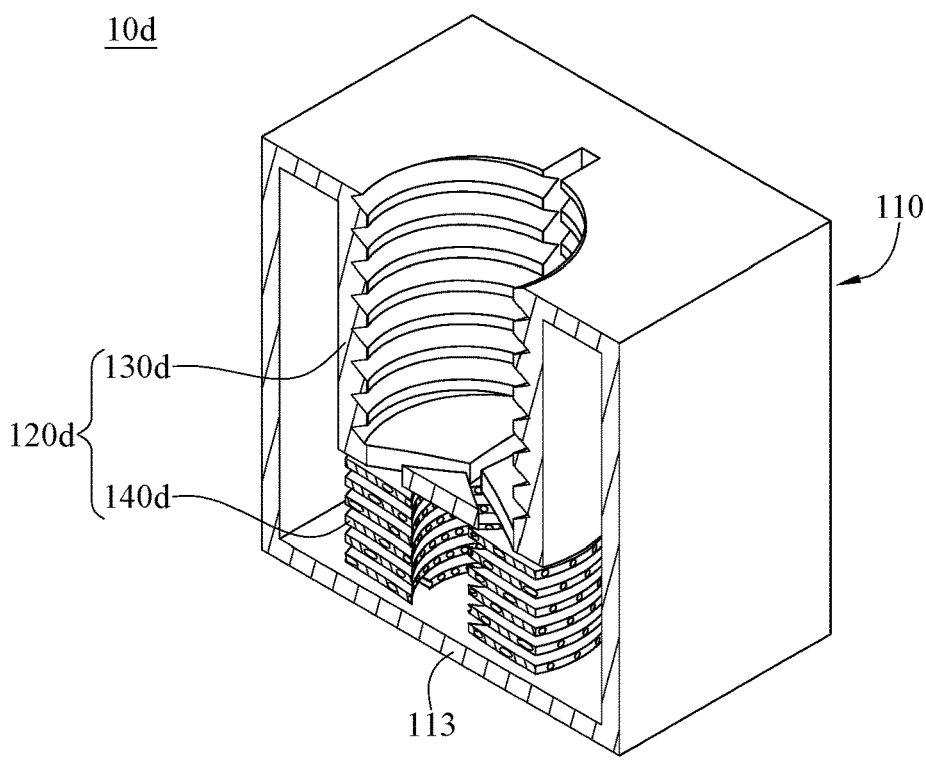
FIG. 6B is a partially cross-sectional perspective view of the prosthesis unit according to still another embodiment of the disclosure.

The disclosure is either not limited to the aforementioned auxiliary cushioning portion 140c. Referring to FIGS. 6A-6B, a cross-sectional side view and a partially cross-sectional perspective view of a prosthesis unit 10d according to still another embodiment of the disclosure are provided. In this embodiment, there is an auxiliary cushioning portion 140d located under abutment engagement portions 130d of a cushion structure 120d of the prosthesis unit 10d. Note that the main difference between the prosthesis unit 10d of this embodiment and the prosthesis unit 10c of the previous embodiment is the design of the auxiliary cushioning portion 140d, thus only the descriptions of the auxiliary cushioning portion 140d will be illustrated below, and the same and similar parts will not be repeated.

In this embodiment, the auxiliary cushioning portion 140d is, for example, a compression spring. Similarly, the auxiliary cushioning portion 140d is able to position the abutment engagement portions 130d in the main part 110 and is also able to absorb and reduce the impact or vibration to the abutment engagement portions 130d.

In more detail, in this embodiment, the auxiliary cushioning portion 140d has pores (not numbered). The pores make the auxiliary cushioning portion 140d more lightweight, and its size, shape, and distribution relate to the required elasticity of the auxiliary cushioning portion 140d. Note that the pores are optional. In some other embodiment, the aforementioned auxiliary cushioning portion 140c may have pores; in yet some other embodiment, the auxiliary cushioning portion 140d may not have pores.

Further, the disclosure is not limited to the configuration of the auxiliary cushioning portion 140d shown in the drawing. In some other embodiments, the auxiliary cushioning portion 140d may be in a form of a conical compression spring, an hourglass compression spring, or any other suitable compression spring.

Figure 7A:
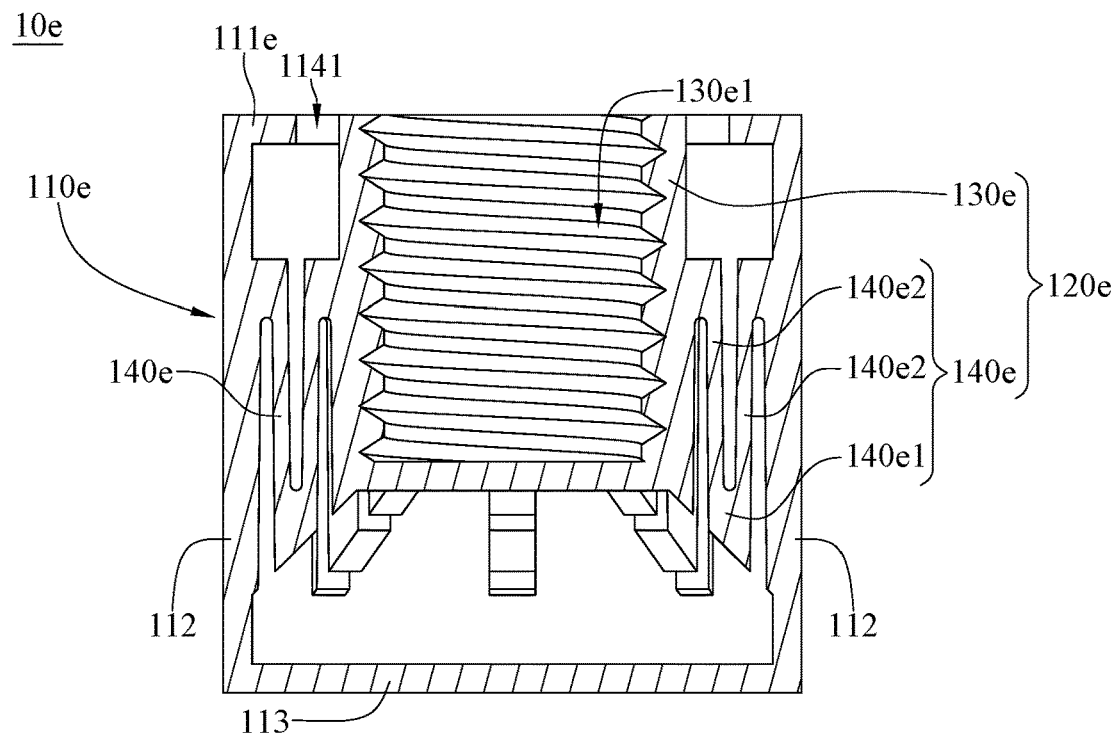
FIG. 7A is a cross-sectional side view of a prosthesis unit according to further another embodiment of the disclosure.
Figure 7B:
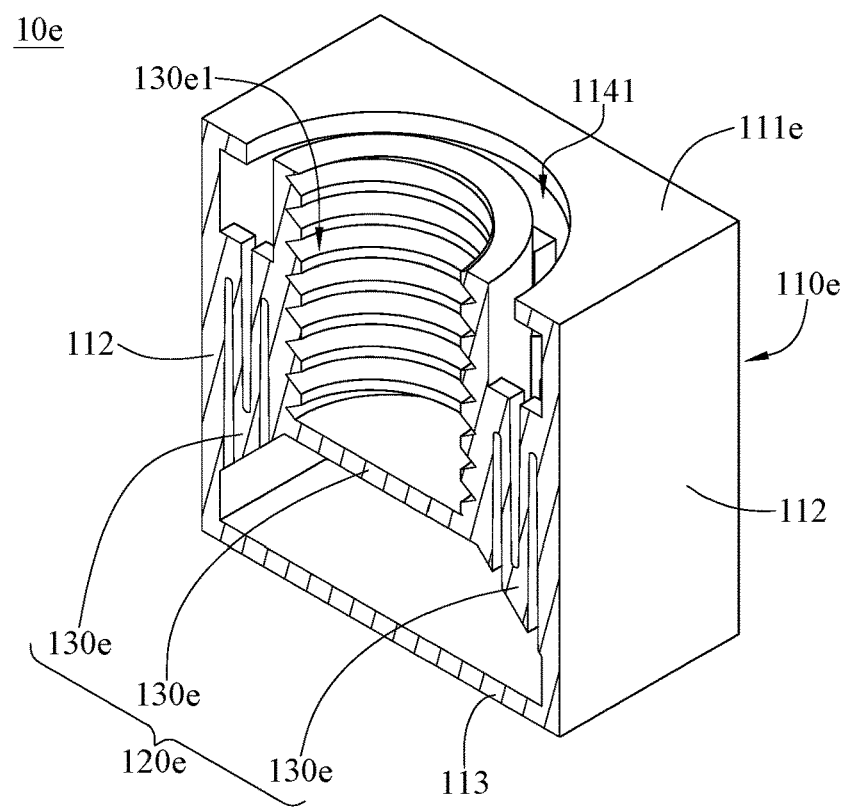
FIG. 7B is a partially cross-sectional perspective view of the prosthesis unit according to further another embodiment of the disclosure.

The location of the auxiliary cushioning portion is not limited. For example, please see FIGS. 7A-7B, a cross-sectional side view and a partially cross-sectional perspective view of a prosthesis unit 10e according to further another embodiment of the disclosure are provided. In this embodiment, a cushion structure 120e of the prosthesis unit 10e only includes a single abutment engagement portion 130e which is a hollow cylindrical; that is, an abutment mounting hole 130e1 is defined by a single abutment engagement portion 130e. Further, the cushion structure 120e further includes at least two auxiliary cushioning portions 140e, each auxiliary cushioning portion 140e is connected to and located between the abutment engagement portion 130e and the side plate 112 of the main part 110e, such that the abutment engagement portion 130e is suspended in the main part 110e.

As shown, in this embodiment, a top plate of the main part 110e has a hole 1141 exposing the abutment engagement portion 130e in the main part 110e, and the abutment engagement portion 130e is suspended at the hole 1141. In addition, in this embodiment, the auxiliary cushioning portion 140e is, for example, a serpentine structure that is flexible and compressible. Specifically, each auxiliary cushioning portion 140e includes a plurality of bend portions 140e1 and a plurality of suspended portions 140e2, where the suspended portions 140e2 are interconnected by the bend portions 140e1 at opposite ends so that the bend portions 140e1 and the suspended portions 140e2 together form a serpentine configuration capable of functioning as a compression spring. Similarly, the auxiliary cushioning portion 140e is able to position the abutment engagement portion 130e with respect to the main part 110e and is also able to absorb and reduce the impact or vibration to the abutment engagement portion 130e.

Figure 8:
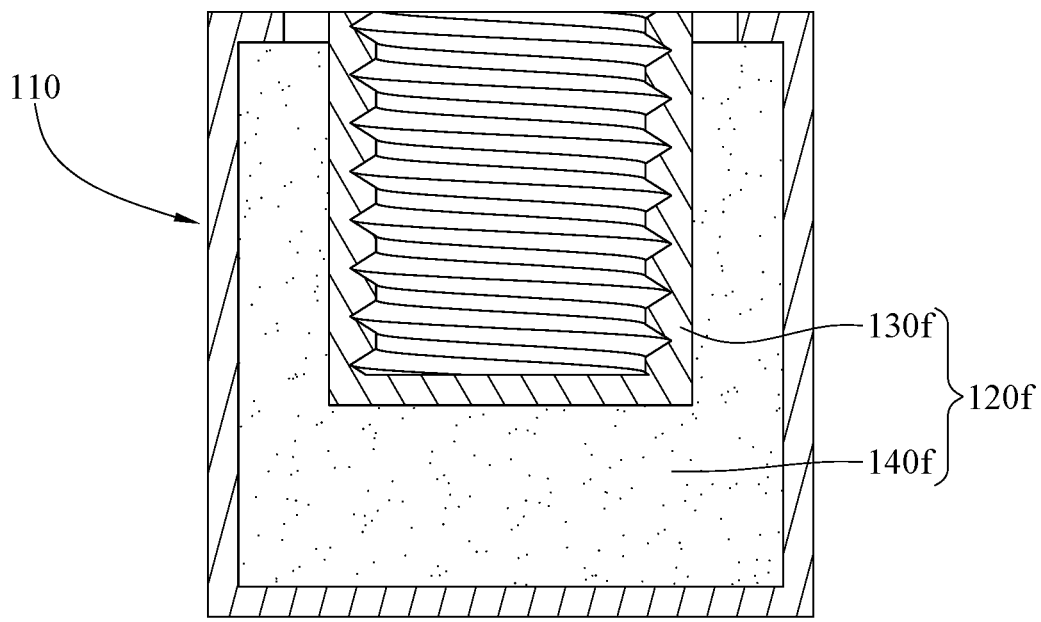
FIG. 8 is a cross-sectional side view of a prosthesis unit according to still further another embodiment of the disclosure.

Alternatively, please see FIG. 8, where FIG. 8 is a cross-sectional side view of a prosthesis unit 10f according to still further another embodiment of the disclosure. In this embodiment, an abutment engagement portion 130f of a cushion structure 120f of the prosthesis unit 10f may have the same or similar configuration as that of the abutment engagement portion 130e in the previous embodiment, but an auxiliary cushioning portion 140f of the cushion structure 120f is a porous filler filled in the room defined by the abutment engagement portion 130f and the inner walls (not numbered) of the main part 110. The auxiliary cushioning portion 140f may be formed by 3D printing and made of titanium alloy, iron-based alloy, cobalt alloy, polymer material, ceramic or composite material thereof, and the auxiliary cushioning portion 140f has a certain degree of compressibility and elasticity. Similarly, the auxiliary cushioning portion 140f is able to position the abutment engagement portions 130f in the main part 110e and is also able to absorb and reduce the impact or vibration to the abutment engagement portions 130f.

The above are the exemplary embodiments of the reconstruction prosthesis that have the cushion structure disposed under the abutment. According to the result of the mechanical test under the rules of artificial natural tooth root of ISO 14801, the reconstruction prostheses of the previous embodiments all have a significant reduction in stress concentration in various stress simulation experiments (e.g., 5 million times dynamic compression fatigue tests under different pressures), having excellent durability to withstand impact and vibration.

Note that, in accordance with the spirit of the disclosure, the details or structure of the aforementioned embodiment can be appropriately adjusted or modified, such as combining the features of different embodiments of the disclosure. For example, in some other embodiments, the auxiliary cushioning portion 140c in FIG. 5A, the auxiliary cushioning portion 140d in FIG. 6A, the auxiliary cushioning portion 140e in FIG. 7A, or the auxiliary cushioning portion 140f in FIG. 8 may be applied to the prosthesis unit 10b in FIG. 4A; alternatively, the auxiliary cushioning portion 140c in FIG. 5A, the auxiliary cushioning portion 140d in FIG. 6A, or the auxiliary cushioning portion 140f in FIG. 8 may be applied to the prosthesis unit 10e in FIG. 7A; or, as long as it helps to position the abutment engagement portion and achieve the required cushioning effect, the auxiliary cushioning portion 140c in FIG. 5A and the auxiliary cushioning portion 140d in FIG. 6A may be arranged between the abutment engagement portion and the side plate of the main part.

According to the reconstruction prosthesis as discussed in the above embodiments of the disclosure, since the reconstruction prosthesis is an assembly of a required number of prosthesis units connected in series, which facilitates the operation of the reconstructive surgery.

Also, each prosthesis unit has a cushion structure movably located at the abutment insertion opening to function as a natural tooth root, thus the prosthesis unit is able to absorb and reduce the impact and vibration due to dental implant surgery or occlusal loading. Therefore, the reconstruction prosthesis can be used for a long time and would not be easily damaged, deformed, dislocated or cause stress concentration, thereby maintaining the required chewing ability.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A reconstruction prosthesis, comprising:
   a plurality of prosthesis units connected in series, each of the plurality of prosthesis units comprising:
   a main part, having an abutment insertion opening and an accommodation space; and
   a cushion structure, integrally formed with the main part and extends into the accommodation space from the abutment insertion opening, wherein the cushion structure is deformable with respect to the main part and comprises a plurality of abutment engagement portions separated from each other and together define an abutment mounting hole extending inwards from the abutment insertion opening;
   wherein each of the plurality of abutment engagement portions comprises a lateral portion extending from the abutment insertion opening and a bottom portion extending from the lateral portion and configured to support an abutment in the abutment mounting hole, and a gap is formed between any adjacent two of the plurality of abutment engagement portions and extends from the lateral portion to the bottom portion.

2. The reconstruction prosthesis according to claim 1, wherein each of the plurality of abutment engagement portions has an internal thread formed on the lateral portion, and the internal threads of the plurality of abutment engagement portions surround the abutment mounting hole.

3. The reconstruction prosthesis according to claim 1, wherein each of the plurality of abutment engagement portions has an inwardly protrusion formed on the lateral portion and located in the abutment mounting hole, and the inwardly protrusion has a guide slant located at a side of the inwardly protrusion facing the abutment insertion opening.

4. The reconstruction prosthesis according to claim 1, wherein the cushion structure further comprises at least one auxiliary cushioning portion connected to and located between the plurality of abutment engagement portions and the main part.

5. The reconstruction prosthesis according to claim 4, wherein the at least one auxiliary cushioning portion is a compression spring.

6. The reconstruction prosthesis according to claim 4, wherein the at least one auxiliary cushioning portion is a serpentine structure comprising a plurality of bend portions and a plurality of suspended portions that are connected in series.

7. The reconstruction prosthesis according to claim 1, wherein the cushion structure further comprises an auxiliary cushioning portion filled in a room defined by the plurality of abutment engagement portions and the main part.

8. The reconstruction prosthesis according to claim 1, wherein the cushion structure comprises a plurality of auxiliary cushioning portions, and the abutment engagement portion is suspended in the accommodation space of the main part via the plurality of auxiliary cushioning portions.

9. The reconstruction prosthesis according to claim 8, wherein each of the plurality of auxiliary cushioning portions is a serpentine structure comprising a plurality of bend portions and a plurality of suspended portions which are connected in series.

10. The reconstruction prosthesis according to claim 1, wherein each of the plurality of prosthesis units further comprises a first engagement portion and a second engagement portion, the first engagement portion and the second engagement portion are a convex structure and a mating concave structure, wherein the first engagement portion of one of the plurality of prosthesis units is detachably engaged with the second engagement portion of another one of the plurality of prosthesis units.

11. The reconstruction prosthesis according to claim 1, wherein the main part further has at least one reconstruction plate mounting hole configured to be fixed with a reconstruction plate which is configured to fix the plurality of prosthesis units together.

12. The reconstruction prosthesis according to claim 1, wherein the main part further has at least one screw hole configured to be fixed with a connecting component which is configured to fix two of the plurality of prosthesis units to each other.

* * * * *